United States Patent

Suzuki et al.

[11] Patent Number: 6,067,841
[45] Date of Patent: May 30, 2000

[54] METHOD OF DETECTING ELEMENT RESISTANCE OF GAS CONCENTRATION SENSOR

[75] Inventors: Toshiyuki Suzuki, Handa; Eiichi Kurokawa, Okazaki; Satoshi Hada, Kariya; Satoshi Haseda, Okazaki; Norio Suzuki, Wakou, all of Japan

[73] Assignees: Denso Corporation; Honda Giken Kogyo Kabushiki Kaisha, both of Japan

[21] Appl. No.: 09/064,784

[22] Filed: Apr. 23, 1998

[30] Foreign Application Priority Data

Apr. 25, 1997 [JP] Japan .................................. 9-109372
Mar. 17, 1998 [JP] Japan .................................. 10-66561

[51] Int. Cl.[7] ............................. G01N 7/00; G01N 27/26; G01L 3/26; F02D 41/00
[52] U.S. Cl. ..................... 73/23.32; 73/117.3; 204/424; 123/688
[58] Field of Search .................... 73/23.32, 23.2, 73/118.1, 117.3; 204/424, 425; 205/784.5, 785; 123/688, 479

[56] References Cited

U.S. PATENT DOCUMENTS

| | | | |
|---|---|---|---|
| 4,114,372 | 9/1978 | Ikeura ........................... | 60/276 |
| 4,419,190 | 12/1983 | Dietz et al. . | |
| 4,543,176 | 9/1985 | Harada et al. . | |
| 4,626,338 | 12/1986 | Kondo et al. ..................... | 204/406 |
| 5,405,521 | 4/1995 | Nakamori et al. ................. | 204/425 |
| 5,547,552 | 8/1996 | Hasegawa et al. ................. | 204/406 |
| 5,719,778 | 2/1998 | Suzumura et al. ................. | 700/207 |
| 5,781,878 | 7/1998 | Mizoguchi et al. ................ | 701/109 |
| 5,810,997 | 9/1998 | Okazaki et al. ................ | 205/784.5 |
| 5,833,836 | 11/1998 | Takami et al. ................... | 205/785 |
| 5,852,228 | 12/1998 | Yamashita et al. ................ | 73/23.32 |

FOREIGN PATENT DOCUMENTS 59-163556 9/1984 Japan .
2290 618 1/1996 United Kingdom .

*Primary Examiner*—Hezron Williams
*Assistant Examiner*—Jay L. Politzer
*Attorney, Agent, or Firm*—Nixon & Vanderhye P.C.

[57] ABSTRACT

A method that detects an air-fuel ratio in each cylinder of an internal combustion engine by properly setting a cycle of detecting an element resistance of an A/F oxygen concentration sensor. Although an actual A/F signal is at the stoichiometric ratio in each cylinder at exhaust timing cycle in a practical engine rotational speed range, the ratio is largely deviated to the rich side in the #1 cylinder. The first element resistance detection timing cycle coincides with generation timing of the actual A/F signal, so that the A/F signal cannot be detected. When the element resistance detection timing cycle is preset so as to be longer than the exhaust timing cycle, the second actual A/F signal detection timing for the #1 cylinder does not coincide with the element resistance detection timing. Consequently, the actual A/F signal of the #1 cylinder can be detected as an A/F signal by the A/F sensor.

18 Claims, 4 Drawing Sheets

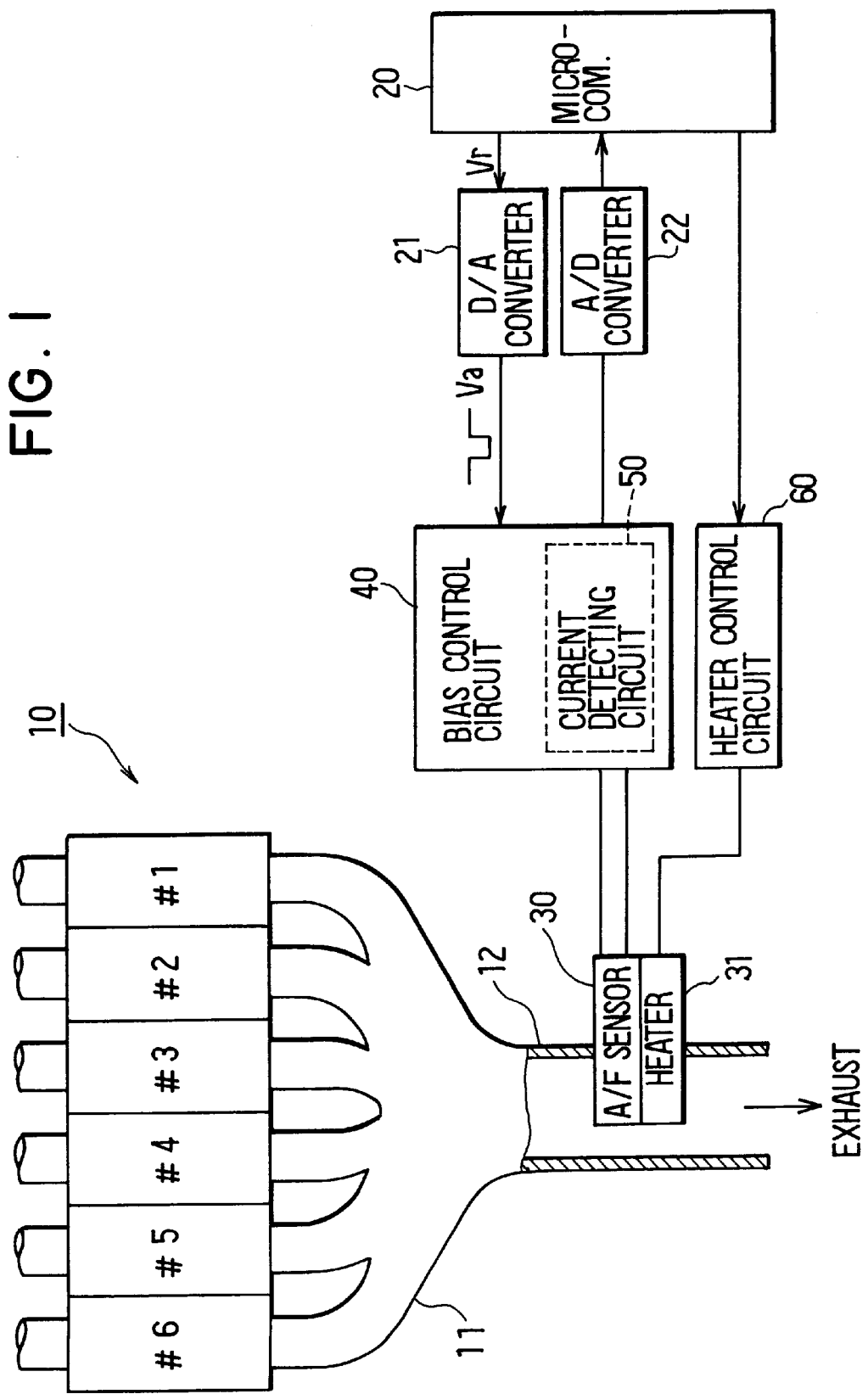

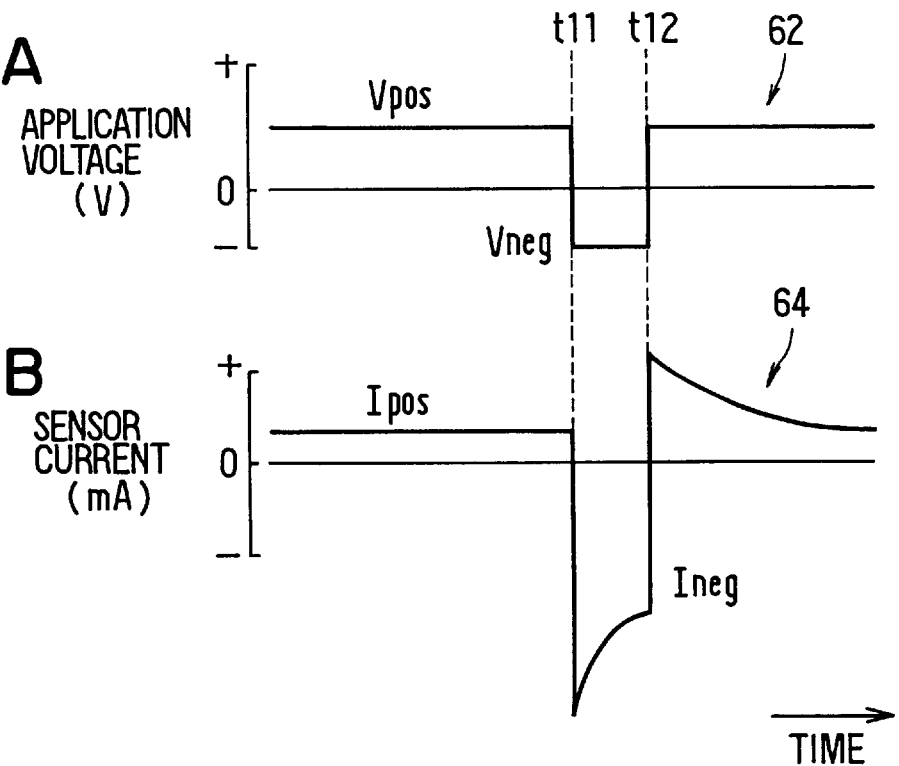

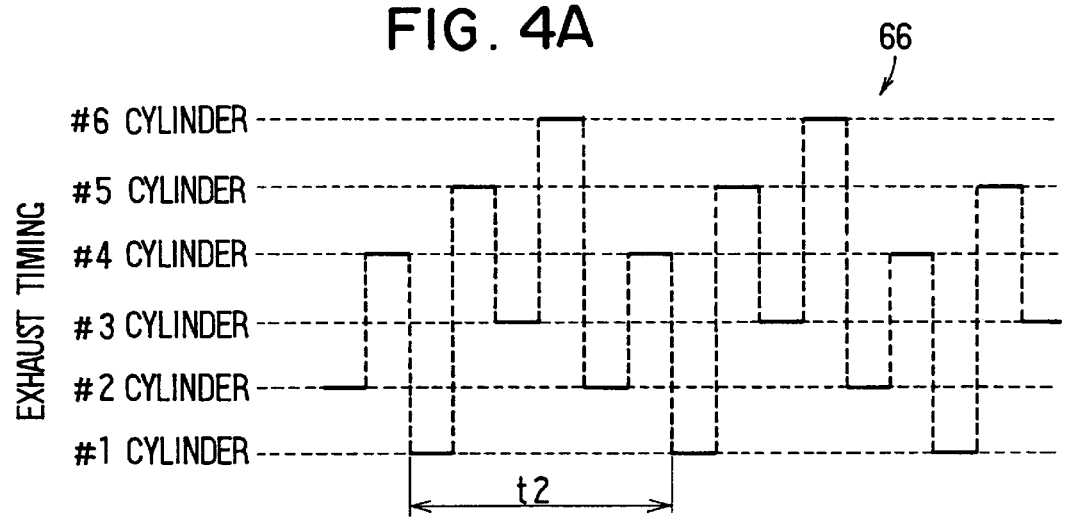
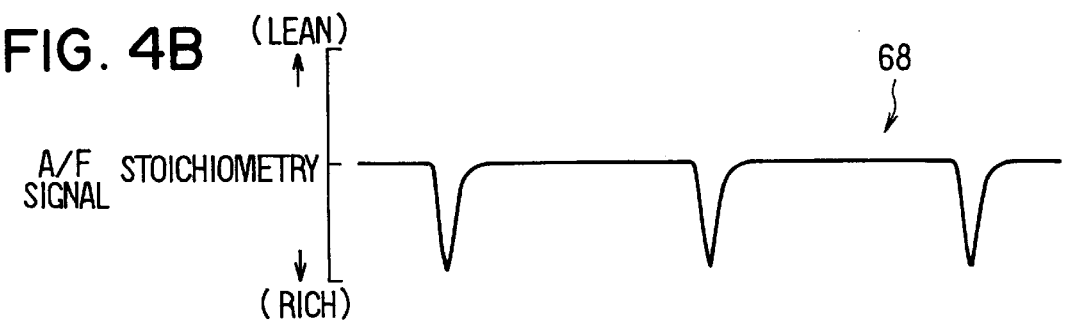
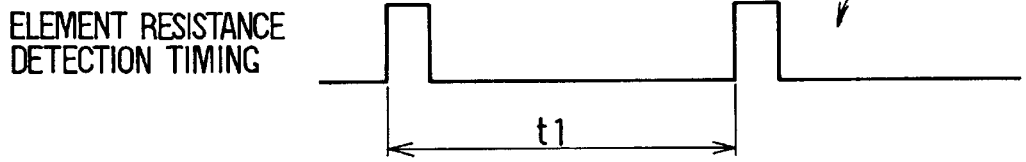
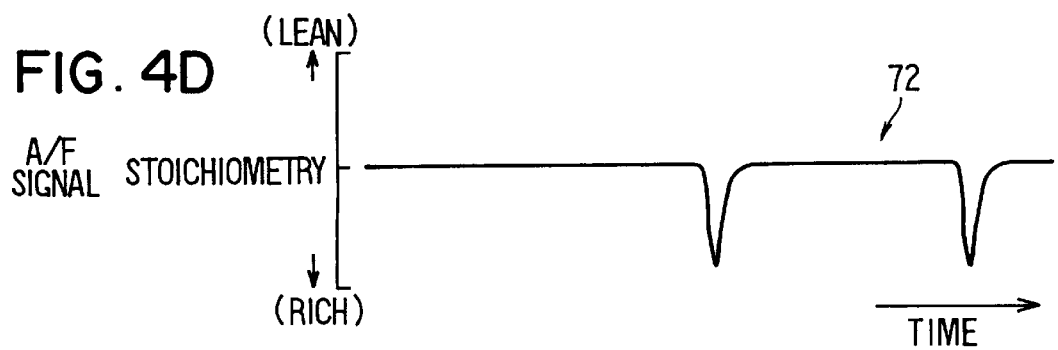

METHOD OF DETECTING ELEMENT RESISTANCE OF GAS CONCENTRATION SENSOR

CROSS-REFERENCE TO RELATED APPLICATION

This application is related to Japanese Patent Application Nos. Hei 9-109372 filed on Apr. 25, 1997 and Hei 10-66561 filed on Mar. 17, 1998, the contents of which are hereby incorporated by reference.

BACKGROUND OF THE INVENTION

1. Field of the Invention

The present invention relates to a method of detecting an element resistance of a gas concentration sensor that detects the concentration of a gas in the exhaust of a vehicle internal combustion engine via a voltage-current frequency characteristic.

2. Description of Related Art

There have been demands in recent years for improved control accuracy in the air-fuel ratio control of motor vehicle engines to maintain engines in a lean-burn state. In response to these demands, a linear air-fuel ratio sensor, or oxygen-concentration sensor, for detecting the air-fuel ratio of mixed air linearly supplied to an internal combustion engine over a wide zone, has been developed and utilized. With such an air-fuel ratio sensor, it is important to keep the air-fuel ratio sensor in an active state to ma the sensor's detection accuracy. This is typically accomplished by electrically controlling a heater attached to the air-fuel ratio sensor to heat a sensor element of the air-fuel ratio sensor to thereby maintain the active state.

To electrically control the heater, conventional techniques detect the temperature of the sensor element and execute a feedback-based control method so that the element temperature is a desired active temperature (for example, about 700° C.). A temperature sensor is attached to the sensor element, and the element temperature is periodically derived from the detection result of the temperature sensor. However, the temperature sensor adds significant cost to the air-fuel ratio sensor. For example, in Japanese Patent Laid-Open No. Sho 59-163556, the sensor element resistance is measured, as the resistance of the sensor element has a predetermined corresponding relation with the element temperature. The element temperature is derived from the detected element resistance.

The time of the element resistance detection has a predetermined cycle. When the cycle continuously coincides with a cycle of the air-fuel ratio detection of a specific cylinder of a multi-cylinder internal combustion engine having at a practical engine rotational speed, a fluctuation in output of the air-fuel ratio in a transition state at a time of combustion in the specific cylinder cannot be detected.

SUMMARY OF THE INVENTION

The present invention solves the above-described limitations. It is an object to provide a method of detecting an element resistance of a gas concentration sensor which can accurately detect the air-fuel ratio in each of the cylinders of an internal combustion engine by properly setting a detection cycle of the element resistance of the gas concentration sensor.

According to the method of the present invention, the oxygen concentration can be detected continuously at the exhaust timing in a specific cylinder in a practical engine rotational speed range of the internal combustion engine. Consequently, the gas concentration of each of the cylinders of the internal combustion engine may be accurately detected, and air-fuel ratio control can be performed for all cylinders.

Also, the gas concentration typically cannot be accurately detected when the element temperature of the gas concentration sensor is low and the gas concentration sensor is in an inactive state. The method of the present invention overcomes the above limitation by changing the execution timing of the element resistance detection to a rate that is faster than the rate in an active state. Electric control of a heater attached to the gas concentration sensor is given priority; thus, an active state can be promptly obtained while the element temperature of the gas concentration sensor is accurately monitored.

BRIEF DESCRIPTION OF THE DRAWINGS

FIG. 1 is a schematic diagram showing the configuration of an air-fuel ratio detecting apparatus to which a method of detecting an element resistance of an A/F sensor according to the present invention is applied;

FIGS. 2A–2B are waveform charts showing the relation between a voltage applied to the A/F sensor and a sensor current in FIG. 1;

FIG. 3 is a flow diagram showing a control routine in a microcomputer used in the method of detecting the element resistance of the A/F sensor according to the present invention;

FIGS. 4A–4D are timing diagrams showing the operation of the air-fuel ratio detecting apparatus to which the method of detecting the element resistance of the A/F sensor according to the present invention is applied.

DETAILED DESCRIPTION OF THE PREFERRED EMBODIMENTS

Figure 5:
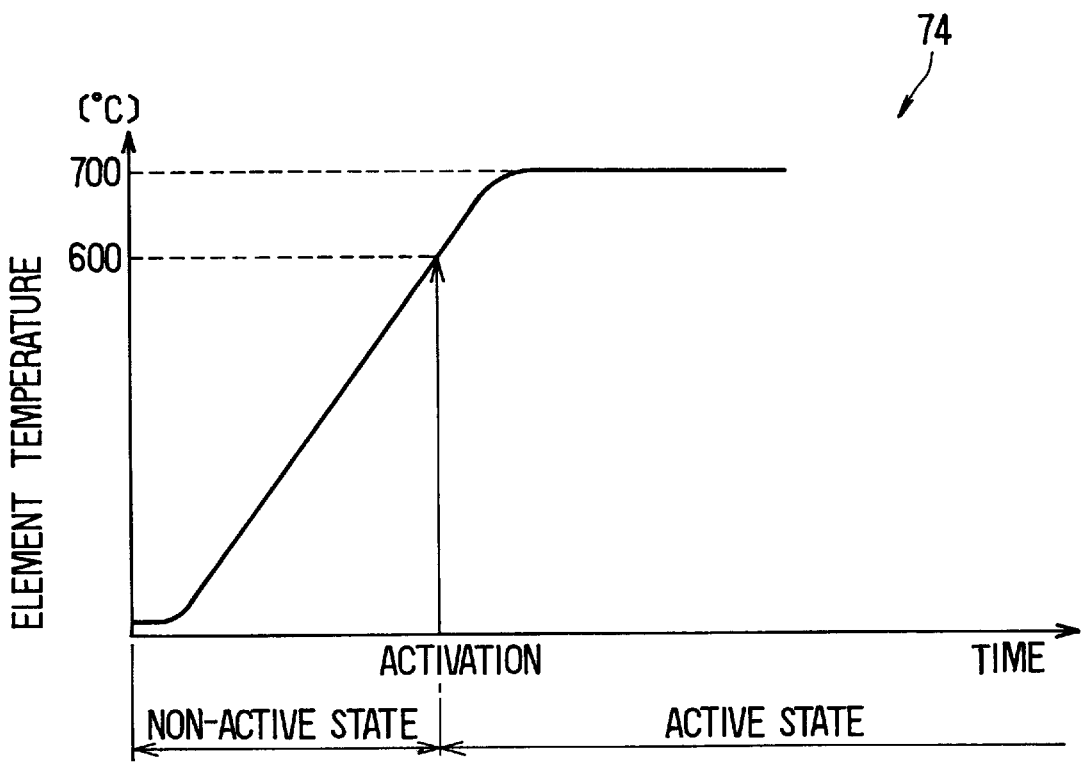
FIG. 5 is a timing diagram showing a transition state of the element temperature in the A/F sensor of the air-fuel ratio detecting apparatus to which the method of detecting the element resistance of the A/F sensor according to the present invention is applied.

A mode for carrying out the invention will be described hereinbelow on the basis of the following disclosed embodiment equivalents thereof. In the following embodiment, reference will be made to cases where the gas concentration sensor according to the present invention is used as an oxygen concentration sensor for detecting the concentration of oxygen (in the exhaust gas of an on-vehicle internal combustion engine).

FIG. 1 is a schematic diagram showing the configuration of an air-fuel ratio detecting apparatus to which a method of detecting an element resistance of an oxygen concentration sensor according to the present invention is applied. The air-fuel ratio detecting apparatus according to the present invention is used for a multi-cylinder electronic control fuel injection system of a motor vehicle internal combustion engine to obtain a desired air-fuel ratio by increasing or decreasing an injection amount of a fuel supplied to each of cylinders of the internal combustion engine based on the detection results of the air-fuel ratio detecting apparatus. A procedure for detecting the element resistance will be described hereinbelow.

In FIG. 1, the air-fuel ratio detecting apparatus has a limit-current type air-fuel ratio sensor (hereinbelow, described as "A/F sensor") 30 as an oxygen concentration sensor. The A/F sensor 30 is attached to an exhaust path 12, which is connected to the downstream side of an exhaust manifold 11 for collecting exhaust gas from cylinders (#1 cylinder to #6 cylinder) of an internal combustion engine 10. A linear air-fuel ratio detection signal corresponding to the oxygen concentration in the exhaust gas is generated from the A/F sensor 30 on application (impression) of a voltage based on instructions from a microcomputer 20. The microcomputer 20 includes a central processing unit (CPU) for executing various known operating processes, a ROM in which a control program is stored, a RAM for storing various data, a B/U (backup) RAM, and other known components. The microcomputer controls a bias control circuit 40 and a heater control circuit 60 in accordance with a predetermined control program.

A bias instruction signal $V_r$, which is preferably a digital signal, for applying (impressing) a voltage to the A/F sensor 30 is supplied from the microcomputer 20 to a D/A converter 21, and is converted to an analog signal $V_a$ by the D/A converter 21. The resultant signal is inputted to the bias control circuit 40. Either a detection voltage indicating the A/F ratio or a detection, voltage of the element resistance is applied from the bias control circuit 40 to the A/F sensor 30.

The bias control circuit 40 detects a sensor current which flows upon application of the voltage to the A/F sensor 30 by a current detection circuit 50. An analog signal of a current value detected by the current detection circuit 50 is supplied to the microcomputer 20 via an A/D converter 22. Operation of a heater 31, which is attached to the A/F sensor 30, is controlled by the heater control circuit 60. That is, in the heater control circuit 60, the duty ratio of an electric power supplied from a battery power source (not shown in the diagram) to the heater 31 is controlled in accordance with the element temperature and the heater temperature of the A/F sensor 30. Therefore, the heating operation of the heater 31, is controlled.

FIGS. 2A and 2B are waveform charts of a sensor current [mA] from the A/F sensor 30 detected by the current detection circuit 50 in the bias control circuit 40 in response to the voltage [V] applied to the A/F sensor 30.

During detection of the A/F ratio before time t11 or after time t12 as shown at 62 in FIG. 2A, a positive application voltage $V_{pos}$ for A/F detection is applied to the A/F sensor 30 in response to the A/F at that time. As shown at 64 in FIG. 2B, the A/F ratio is obtained from a sensor current $I_{pos}$ generated from the A/F sensor 30 in response to the application voltage $V_{pos}$. At the time of the element resistance detection between time t11 and time t12 as shown in FIG. 2A, a negative application voltage $V_{neg}$, having a single and predetermined time constant as a predetermined frequency signal, is applied. As shown in FIG. 2B, a sensor current $I_{neg}$, generated from the A/F sensor 30 in response to the application voltage $V_{neg}$, is detected. By dividing the application voltage $V_{neg}$ by the sensor current $I_{neg}$ at that time, an element resistance ZDC is obtained (ZDC=$V_{neg}/I_{neg}$).

The operation of the air-fuel ratio detecting apparatus constructed as mentioned above will be described.

FIG. 3 is a flow diagram showing a control routine for the microcomputer 20. The control routine is activated upon the supply of electric power to the microcomputer 20.

In FIG. 3, the routine determines at Step S100 whether a predetermined time T1 has elapsed since the previous A/F detection. The predetermined time T1 corresponds to the A/F detection cycle. When the predetermined time T1 has elapsed since the previous A/F detection, the processing routine advances to step S200. A sensor current (limit current) detected by the current detection circuit 50 is read and the A/F ratio of the internal combustion engine 10 corresponding to the sensor current at that time is detected by using a characteristic map (not shown) preliminarily stored in the ROM.

The processing routine then advances to step S300 and determines whether a predetermined time T2 has elapsed since the previous element resistance detection. The predetermined time T2 corresponds to the detection cycle of the element resistance. If time T2 has not elapsed, steps S100 to S300 are repeated, and the A/F ratio is detected at the end of each predetermined time T1. When the discriminating condition of step S300 is satisfied, and the predetermined time T2 has elapsed since the previous detection of the element resistance, the processing routine advances to step S400. At step S400 an element resistance detecting process as described above is executed. After that, the processing routine is returned to step S100, and is repeated.

FIGS. 4A–4D are timing diagrams showing various signal detection timings with respect to the exhaust timing of each of the cylinders in the air-fuel ratio detecting apparatus, to which the present method of detecting sensor element resistance is applied.

In FIG. 4A, a cycle t2 is shown at 66 in a practical engine rotational speed range of each cylinder (#1 cylinder to #6 cylinder) of the internal combustion engine 10. Exhaust timing is shown in this example when the rotational speed at the time of idling is 700 rpm, although an actual A/F signal shown at 68 in FIG. 4B is at the stoichiometric ratio in the #2 to #6 cylinders, and the timing of the #1 cylinder is largely deviated to the rich side. In the present example, as shown at 70 in FIG. 4C, the first element resistance timing cycle t1 coincides with the timing of the actual A/F signal. The A/F sensor 30 consequently cannot detect the actual A/F signal of the #1 cylinder, which is largely deviated to the rich side, and regards that the A/F signal is at the stoichiometric ratio as shown at 72 in FIG. 4D.

When the cycle t1 of the element resistance detection timing is preliminarily set to a value greater than the cycle t2, for example, 180 ms or longer, that is, when the engine rotational speed of the internal combustion engine 10 is about 667 rpm or faster, the second actual A/F signal detection timing for the #1 cylinder does not coincide with the element resistance detection timing. The actual A/F signal of the #1 cylinder can be therefore detected as an A/F signal by the A/F sensor 30. After that, although the actual A/F signal detection timing coincides with the element resistance detection timing, the two do not coincide continuously. Consequently, the A/F signal of each of the cylinders of the internal combustion engine 10 can be accurately detected. If the element resistance detection timing is set to a value that is too large, a fluctuation in element temperature easily occurs, and the accuracy of the A/F signal deteriorates. It is therefore preferable to set the cycle so that the A/F control of each cylinder can be realized and the accuracy of the A/F signal does not deteriorate.

According to the method of detecting the element resistance as mentioned above, the current signal according to the A/F ratio of the detected fuel is generated upon the application of a voltage, as described above. Detection of the sensor element resistance is based on the current change accompanying the voltage change and is preferable performed at a cycle of 180 ms. Execution timing is not synchronized twice or more continuously with the exhaust timing of a specific cylinder when the engine speed is 700 rpm or higher. Therefore, the A/F ratio can be detected continuously at the exhaust timing of the specific cylinder in a practical engine speed range. Thus, the A/F ratio of each of the cylinders of the internal combustion engine 10 can be accurately detected, and the A/F ratio control can be respectively performed on the cylinders.

FIG. 5 shows a time chart at 74 showing a transition state of the element temperature of the A/F sensor 30 at the time of cranking (cold start) of the internal combustion engine 10.

In the foregoing embodiment, as a practical engine rotational speed range of the internal combustion engine 10, 700 rpm or higher is presumed as a rotational speed at the time of idling. When the A/F sensor 30 is in an inactive state, such as during cranking of the internal combustion engine 10 or the like, the maximum element temperature increasing capacity of the heater 31 is used to quickly change the inactive state to an active state (for example, about at 600° C. or higher), and operation is shifted to the A/F ratio control. In such a case, as shown in FIG. 5, the element temperature of the A/F sensor 30 is rapidly increased to about 600° C. in a short time (for example, about 10 seconds). If the execution timing of the element resistance detection is long, the A/F sensor 30 cannot monitor the element temperature sufficiently, so that the element temperature rises too high, or power for the electric control of the heater cannot be properly supplied to the heater 31. Consequently, the A/F sensor 30 may be damaged.

When the A/F sensor 30 is in the inactive state, it is therefore desirable that the execution timing of the element resistance detection is set to a cycle (for example, 90 ms) such that the element temperature can be properly controlled. It is also desirable that the execution timing of the element resistance detection is changed to 180 ms or longer when the A/F sensor 30 becomes active.

As mentioned above, according to the present method of detecting the element resistance of the A/F sensor 30, the execution timing of the element resistance detection is changed in accordance with the active state of the A/F sensor 30. That is, when the element temperature of the A/F sensor 30 is low, and the A/F sensor 30 is in an inactive state at the time of cranking of the internal combustion engine 10, naturally, the A/F cannot be accurately detected. The execution timing of the element resistance detection is therefore set to be more frequent than that in the active state, and the heater 31 attached to the A/F sensor 30 is electrically controlled in a manner as described above. The active state can be, therefore, promptly obtained while the element temperature of the A/F sensor 30 is accurately monitored. When the element temperature of the A/F sensor 30 rises and the active state is obtained, as mentioned above, the execution timing of the element resistance detection of the A/F sensor 30 is changed to 180 ms or longer. Consequently, the A/F detection executed by the A/F sensor 30 can be performed continuously twice or more with respect to the same cylinder.

Although the method of detecting the element resistance of the A/F sensor 30 applied to an air-fuel ratio detecting apparatus has been described in the foregoing embodiment, the invention can be also applied to an internal combustion engine having four cylinders, or any number of cylinders.

Although the internal combustion engine having a rotational speed of 700 rpm at the time of idling is presumed, and the element resistance detection cycle after the activation of the A/F sensor 30 is set to 180 ms or longer in the embodiment described above, the present invention is not limited to these conditions. The detection cycle is preset according to the rotational speed at the time of idling of the internal combustion engine. For example, when the rotational speed at the time of idling is 500 rpm, it is sufficient to set the element resistance detection cycle to 260 ms or longer.

Also, the present invention can be similarly applied in the same way as in the case of the gas or oxygen concentration sensor as a control method for controlling other sensors which are directed to detecting the concentration of gases such as NOx, HC, CO and the like.

What is claimed is:

1. A method of detecting an element resistance of a gas concentration sensor that generates a current signal proportional to a detected gas concentration in exhaust from a multi-cylinder internal combustion engine, comprising the steps of:

sensing a detected gas concentration via a sensor during a gas detection cycle;

selectively changing a voltage provided to the sensor during a sensor resistance detection cycle;

sensing a current change in the sensor resulting from the step of selectively changing a voltage;

detecting resistance of the sensor based on the step of sensing a current change;

controlling timing of the steps of sensing a detected gas concentration and selectively changing a voltage, such that the step of selectively changing a voltage is asynchronous with the step of sensing a detected gas and such that the sensor resistance detection cycle is synchronized one time at most with the exhaust timing cycle of a specific cylinder during an engine firing cycle in the multi-cylinder internal combustion engine.

2. The method of claim 1, further comprising the steps of:

heating the sensor, when the sensor is in an in inactive state, to bring the sensor to an active state temperature; and increasing the element resistance detection cycle, until the sensor reaches the active state, during the step of heating the sensor to provide accurate monitoring of the element resistance.

3. The method of claim 1, wherein the step of sensing a concentration of a detected gas during a gas detection cycle comprises the step of sensing a concentration of oxygen during an exhaust cycle of a multi-cylinder motor vehicle internal combustion engine.

4. The method of claim 1, wherein the step of changing a voltage provided to the sensor during a sensor resistance detection cycle comprises changing the voltage from a positive voltage applied during the gas detection cycle to a negative voltage.

5. The method of claim 1, further comprising the step of setting the gas detection cycle to be shorter than the sensor resistance detection cycle so that the gas detection cycle is repeated a plurality of times for every occurrence of the sensor resistance detection cycle.

6. The method of claim 1, further comprising the step of selectively heating the sensor to maintain the sensor at a predetermined active state operating temperature.

7. The method of claim 6, further comprising the steps of:

monitoring the detected resistance of the sensor to determine whether the sensor temperature is at the predetermined active state operating temperature; and increasing the frequency of the element resistance detection cycle during the step of heating when the sensor temperature is below the active state operating temperature.

8. A method of controlling a gas concentration sensor that generates a current signal proportional to as concentration of a first gas in exhaust from a multi-cylinder internal combustion engine, comprising the steps of:

sensing a concentration of said first gas via a sensor in a detected exhaust gas during an exhaust timing cycle of each cylinder in a multi-cylinder internal combustion engine;

selectively changing voltage provided to the sensor during a sensor resistance detection cycle;

sensing a current change in the sensor resulting from the step of selectively changing voltage;

detecting resistance of the sensor based on the step of sensing a current change; and controlling timing of the steps of sensing a concentration of said first gas and selectively changing voltage, such that the sensor resistance detection cycle is synchronized one time at most with the exhaust timing cycle of a specific cylinder during an engine firing cycle in the multi-cylinder internal combustion engine.

9. The method of claim 8, wherein the steps of sensing a concentration of said first gas comprises the steps of:

sensing a current change in the sensor; and mapping the current value to first gas concentration level according to predetermined parameters.

10. The method of claim 8, further comprising the step of selectively heating the sensor to maintain the sensor at a predetermined active state operating temperature.

11. The method of claim 10, further comprising the steps of:

monitoring the detected resistance of the sensor to determine whether the sensor temperature is at the predetermined active state operating temperature; and increasing the frequency of the element resistance detection cycle during the step of heating when the sensor temperature is below the active state operating temperature.

12. A gas concentration sensor that detects the concentration of a gas in the exhaust from a multi-cylinder internal combustion engine, comprising:

a sensor element located in proximity to a gas supply that generates a current proportional to a detected gas concentration;

a heater located in proximity to the sensor element that heats the sensor element; and a controller that selectively controls operation of the sensor element and the heater;

the controller activating the sensor element to generate the current signal during a gas detection cycle in response to predetermined conditions, the controller also activating the heater to heat the sensor element to a predetermined active state temperature to ensure proper operation of the sensor element;

the controller selectively changing a voltage provided to the sensor element during a sensor element resistance detection cycle, and sensing a resulting current change in the sensor element, to detect a corresponding sensor element resistance;

the controller controlling timing of the gas detection cycle and the sensor element resistance detection cycle such that the gas detection cycle and the sensor element resistance detection cycle occur asynchronously; and the controller controlling timing of activating the sensor element and of selectively changing voltage, such that the sensor resistance detection cycle is synchronized one time at most with the exhaust timing cycle of a specific cylinder during an engine firing cycle in the multi-cylinder internal combustion engine.

13. The sensor of claim 12, wherein the sensor element is operative to detect a concentration of oxygen during an exhaust cycle of a multi-cylinder motor vehicle internal combustion engine.

14. The sensor of claim 12, wherein the controller activates the heater at a maximum heating mode when the sensor element is in an inactive state to cause the sensor to reach an active state.

15. The sensor of claim 14, wherein the controller increases a frequency of the sensor element resistance detection cycle when the heater is at the maximum setting to monitor operation of the heater, and wherein the controller returns the heater to a regular heating mode when the sensor element reaches an active state.

16. The sensor of claim 14, wherein the controller sets the gas detection cycle to be shorter than the sensor resistance detection cycle so that the gas detection cycle is repeated a plurality of times for every occurrence of the sensor element resistance detection cycle.

17. The sensor of claim 14, wherein the sensor element generates a current proportional to a detected gas concentration of one of NOx, HC and CO gases.

18. The sensor of claim 14, wherein the controller includes a gas concentration map that enables the controller to determine an air-fuel ratio based on the current generated at the sensor element.

* * * * *